United States Patent [19]

Selnick et al.

[11] Patent Number: 5,618,830

[45] Date of Patent: Apr. 8, 1997

[54] DIOXOBUTANOIC ACID DERIVATIVES AS INHIBITORS OF INFLUENZA ENDONUCLEASE

[75] Inventors: Harold G. Selnick, Ambler; John J. Baldwin, Gwynedd Valley; Gerald S. Ponticello; Joanne E. Tomassini, both of Lansdale, all of Pa.

[73] Assignee: Merck & Co., Inc., Rahway, N.J.

[21] Appl. No.: 536,294

[22] Filed: Sep. 29, 1995

Related U.S. Application Data

[62] Division of Ser. No. 324,190, Oct. 17, 1994, Pat. No. 5,475,109.

[51] Int. Cl.⁶ .......................... A61K 31/44; A61K 31/445
[52] U.S. Cl. ...................... 514/358; 514/317; 514/318
[58] Field of Search .................. 514/358, 317, 514/318

Primary Examiner—Jerome D. Goldberg
Attorney, Agent, or Firm—Sylvia A. Ayler; Roy D. Meredith; Mark R. Daniel

[57] ABSTRACT

Dioxobutanoic acids substituted with piperidine or similar N-substituted saturated cycloalkyls are found to inhibit the cap-dependent endonuclease of influenza virus. These compounds are useful in the prevention or treatment of infection by influenza virus and the treatment of influenza, either as compounds, pharmaceutically acceptable salts, pharmaceutical composition ingredients, whether or not in combination with other antivirals, immunomodulators, antibiotics or vaccines. Methods of treating influenza and methods of preventing or treating infection by influenza virus are also described.

24 Claims, No Drawings

DIOXOBUTANOIC ACID DERIVATIVES AS INHIBITORS OF INFLUENZA ENDONUCLEASE

This is a division of application Ser. No. 08/324,190 filed Oct. 17, 1994, now U.S. Pat. No. 5,475,109.

The present invention is concerned with compounds which inhibit an endonuclease encoded by influenza virus. The compounds, or pharmaceutically acceptable salts thereof, are of value in the prevention of infection by influenza virus, and the treatment of infection by influenza virus.

The present invention also relates to pharmaceutical compositions containing the compounds and to a method of use of the present compounds and other agents for the treatment of influenza and the viral infection by influenza virus.

BACKGROUND OF THE INVENTION

A myxovirus designated influenza is the etiological agent of the common "flu", an acute highly contagious viral disease characterized by sudden onset, fever, prostration, and progressive intimation of the respiratory mucous membrane.

The compounds of the present invention contain dioxobutanoic acids substituted with piperidine and similar N-substituted saturated cycloalkyls. Applicants demonstrate that the compounds of this invention are inhibitors of the cap-dependent endonuclease of influenza virus. The compounds were shown to be selective for influenza transcription by testing in several related enzyme assays. The compounds were not inhibitory in other polymerase assays including VSV transcription, HIV reverse transcriptase, T7 phage, Hela cell RNA polymerase II and Hela cell DNA polymerase α when tested at concentrations 100–500 fold above the $IC_{50}$ for influenza transcription; thereby showing specific inhibition of influenza transcription. The inhibitory activity was specific to cap-dependent influenza transcription and had no effect upon influenza transcription primed cap-independently with the dinucleotide ApG. The mode of action of the inhibitors was demonstrated to be inhibition of cap-dependent endonuclease activity in an influenza cleavage assay in which the dioxobutanoic acids had $IC_{50}$s similar to those obtained in influenza transcription. Additionally, the inhibitor had no effect upon transcription when primed with capped substrates which did not undergo endonucleolytic processing, further confining inhibition of the influenza endonuclease. The specificity of influenza cleavage inhibition was demonstrated in nuclease counterscreens in which the compound had no effect upon RNases A, T1, U1 and HIV RNase H when tested up to 100-fold above the $IC_{50}$ obtained in influenza cleavage.

BRIEF DESCRIPTION OF THE INVENTION

Compounds of Formula I, as herein defined, are disclosed. These compounds are useful in the inhibition of influenza virus cap-dependent endonuclease, the prevention of infection by influenza virus, and the treatment of infection by influenza virus, either as compounds, pharmaceutically acceptable salts, hydrates or esters, pharmaceutical composition ingredients, whether or not in combination with other antivirals, immunomodulators, antibiotics or vaccines. Methods of treating influenza, methods of preventing infection by influenza virus, and methods of treating infection by influenza virus are also disclosed.

| ABBREVIATIONS | |
|---|---|
| | Activating Agent |
| HBT (HOBT or HOBt) | 1-hydroxybenzotriazole hydrate |
| | Condensing Agent |
| EDC | 1-ethyl-3-(3-dimethylamino-propyl)carbodiimide |

DETAILED DESCRIPTION OF THE INVENTION AND PREFERRED EMBODIMENTS

This invention is concerned with the compounds of Formula I, combinations thereof, or pharmaceutically acceptable salts thereof, in the inhibition of influenza virus transcriptase, the prevention of infection by influenza virus, and the treatment of infection by influenza virus. Compounds of Formula I are defined as follows:

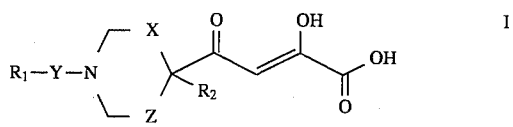

or pharmaceutically acceptable salt, hydrate or crystal form thereof,
wherein:
X is —CH$_2$—, CH$_2$—CH$_2$—, or a bond;
Z is —CH$_2$—, CH$_2$—CH$_2$—, or a bond;
Y is —CH$_2$—, CO, SO$_2$—, or a bond;
R$_1$ and R$_2$ are independently selected from the following: branched or unbranched C$_{1-6}$ alkyl-, C$_{1-6}$ alkyloxy-, —N—C$_{1-6}$ alkyl-, C$_{3-8}$ cycloalkyl-, phenyl, naphthyl, pyridyl, furanyl, thienyl, or quinolinyl, any of which may be substituted once or twice with C$_{1-5}$ alkyl, C$_{3-8}$ cycloalkyl, phenyl, quinolinyl, pyridyl, furanyl, thienyl, C$_{1-6}$-alkoxy, Br, F, or Cl.

The compounds of the present invention may have asymmetric centers and occur as racemates, racemic mixtures and as individual diastereomers, enantiomers, or mixtures of enantiomers with all isomeric forms being included in the present invention.

When any variable (e.g., R$_1$ or R$_2$, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Halo", as used herein, means fluoro, chloro, bromo or iodo.

The pharmaceutically-acceptable salts of the compounds of Formula I (in the form of water- or oil-soluble or dispersible products) include the conventional non-toxic salts or the quaternary ammonium salts of these compounds, which are formed, e.g., from inorganic or organic acids. Examples of such acid addition salts include acetate, adipate, alginate, aspartate, benzoate, bisulfate, citrate, digluconate, dodecylsulfate, fumarate, glycerophosphate, hemisulfate, hydrochloride, 2-hydroxy-ethanesulfonate, lactate, maleate, methanesulfonate, succinate and tartrate.

One preferred embodiment of this invention is compounds of Formula I, wherein

Y is —CH$_2$—;

R$_1$ is
(i) phenyl, unsubstituted or substituted with halo; or
(ii) cyclohexyl;

R$_2$ is
(i) H or
(ii) benzyl, unsubstituted or substituted with halo; or pharmaceutically acceptable salt, hydrate or ester thereof.

Preferred compounds of this invention include the following:

Compound A:

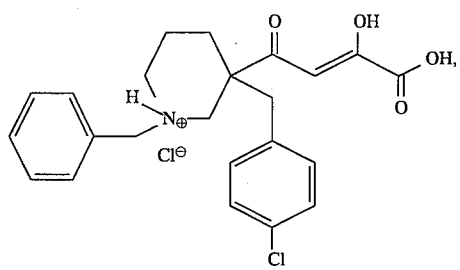

named
4-[N-benzyl-3-(4-chlorobenzyl)piperidin-3-yl]2,4-dioxobutanoic acid hydrochloride,
or pharmaceutically acceptable salt, hydrate or ester thereof;

Compound B:

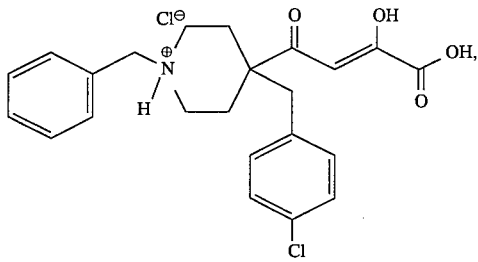

named
4-[N-benzyl-4-(p-chlorobenzyl)piperidin-4-yl]2,4-dioxobutanoic acid hydrochloride,
or pharmaceutically acceptable salt, hydrate or ester thereof;

Compound C:

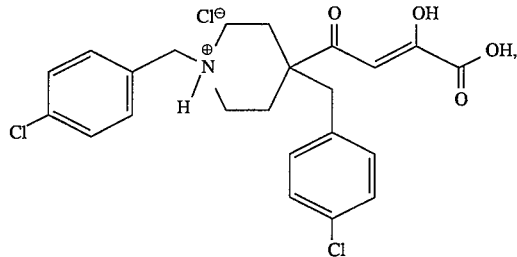

named
4-N-(p-chlorobenzyl)-4-(p-chlorobenzyl)piperidin-4-yl]2,4-dioxobutanoic acid hydrochloride,
or pharmaceutically acceptable salt, hydrate or ester thereof;

Compound D:

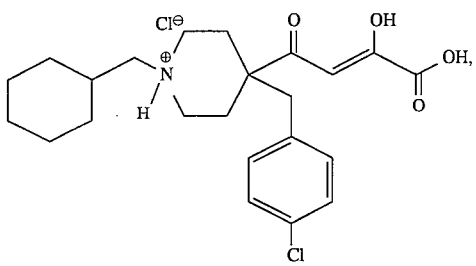

named
4-[1-cyclohexylmethyl-4-(p-chlorobenzyl)piperidin-4-yl]2,4-dioxobutanoic acid hydrochloride,
or pharmaceutically acceptable salt, hydrate or ester thereof.

The compounds of the present invention are prepared in accordance with Schemes I–III.

SCHEME I

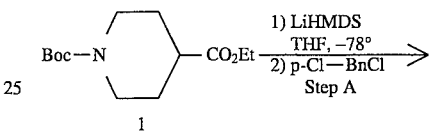

1

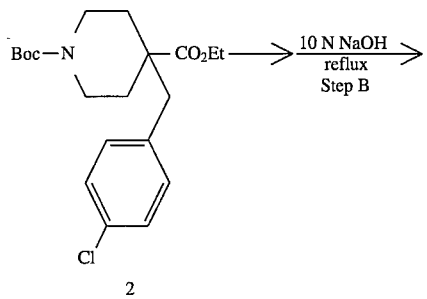

2

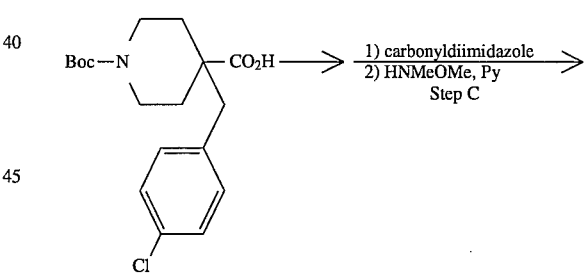

3

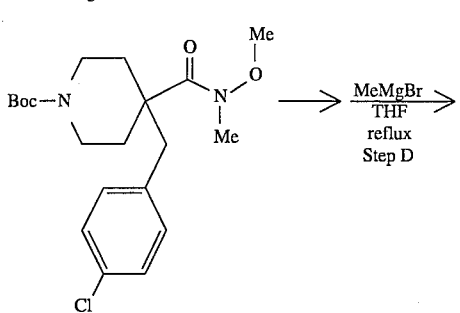

4

-continued
SCHEME I

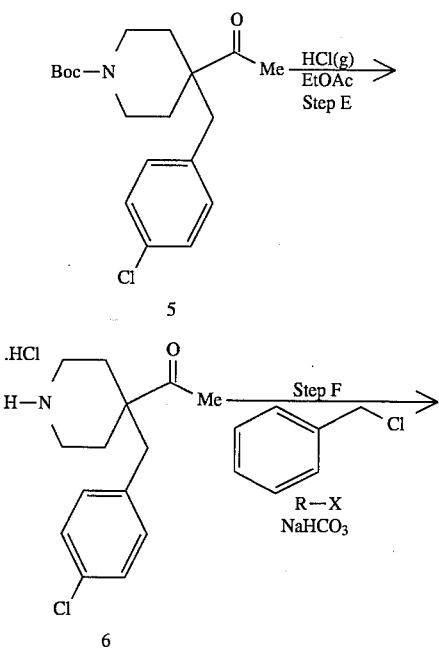

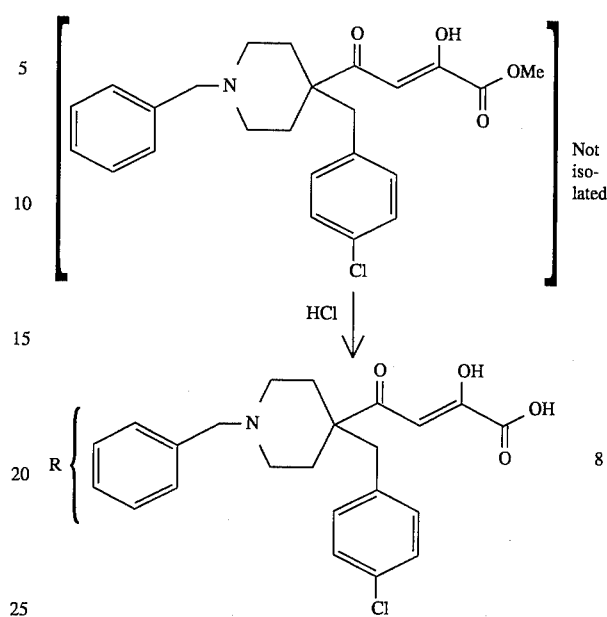

According to Scheme I, the N-protected ester 1 is alkylated with the appropriate halide, e.g., 4-chlorobenzyl chloride, in the presence of an amide base such as LDA or LiHMDS [lithium bis(trimethylsilyl)-amide]. The alkylated ester product 2 is hydrolyzed to a carboxylic acid 3. Reaction with carbonyldiimidazole affords the corresponding substituted acyl imidazole, which reacts with the appropriate amine, e.g., N,O-dimethylhydroxylamine, to give amide 4. Alkylation with Grignard reagent followed by deprotection of the nitrogen results in 6. Amine 6 is alkylated by reaction with a slight excess of halide in base to afford 7. Reaction with an excess of reducing agent and the appropriate oxalic acid gives 8.

Scheme I is illustrated by Example 1, but is not limited to this particular example.

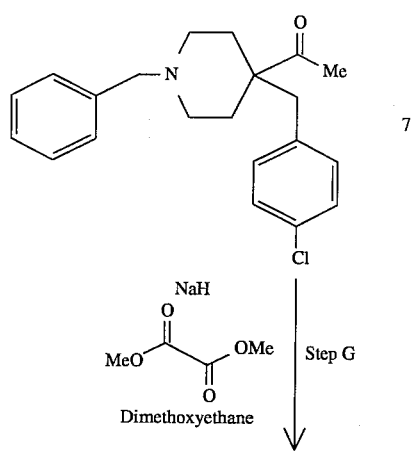

SCHEME II

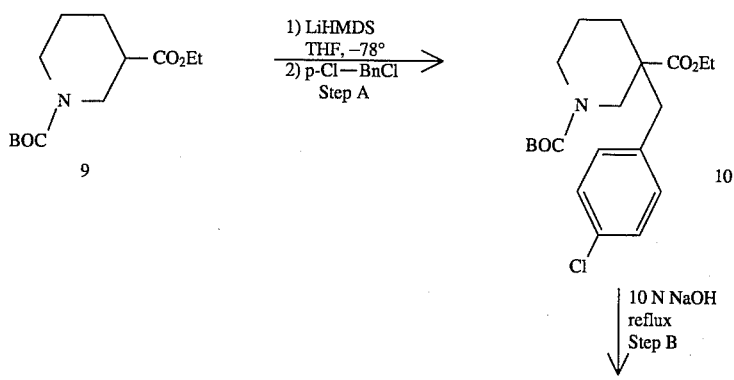

5,618,830
-continued
SCHEME II
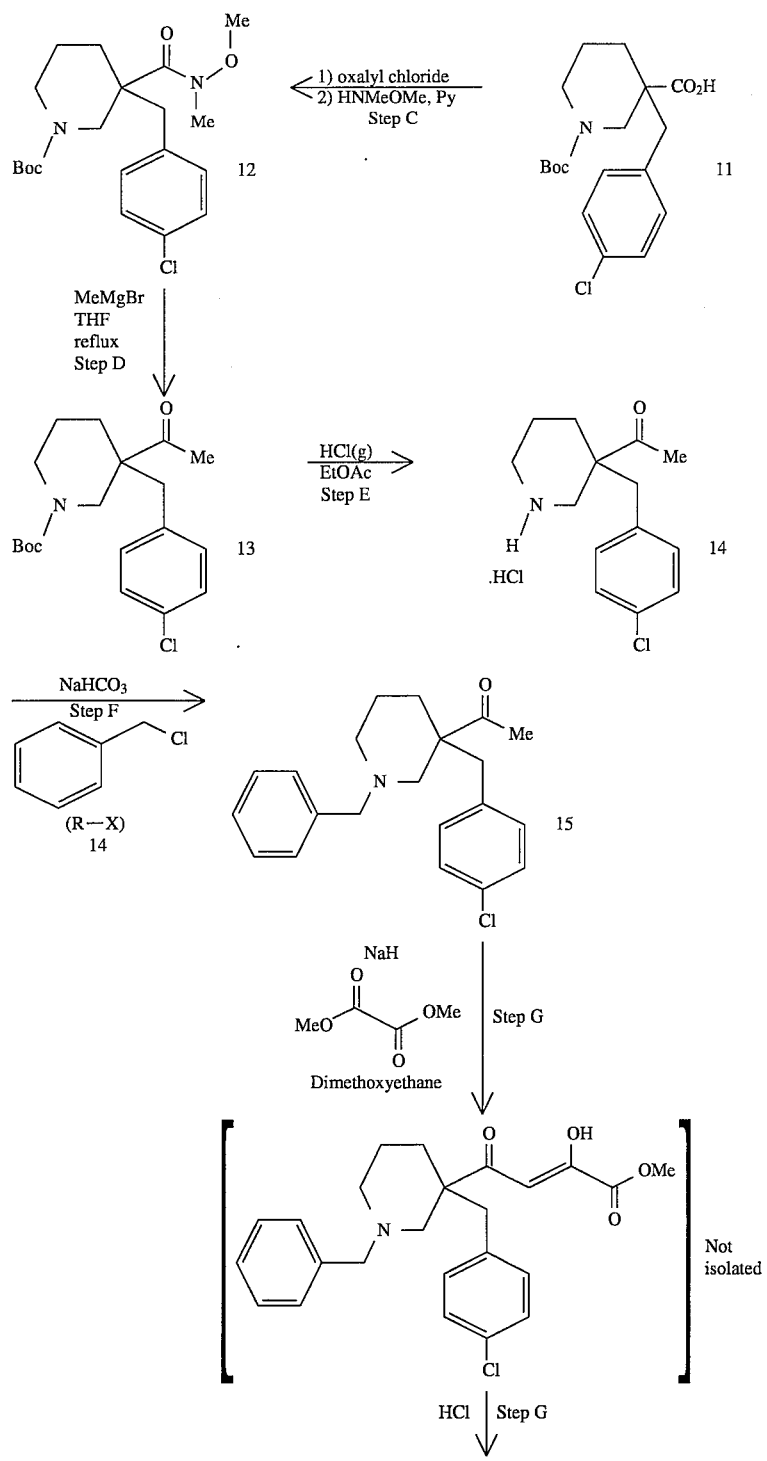

-continued
SCHEME II

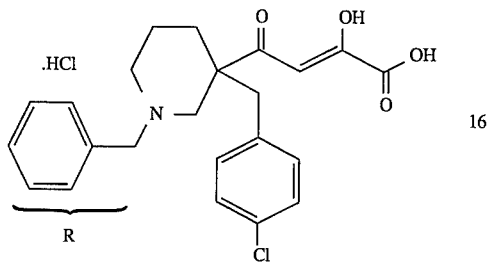

For 3-substituted piperidine compounds of Formula I, Scheme II illustrates a method of synthesis. In Step C, the preferred reagent is oxalylchloride instead of carbonyldiimidazole. Otherwise, synthesis of 3-substituted piperidine compounds of Formula I substantially resembles the synthesis of 4-substituted piperidine compounds of Formula I as set forth in Scheme I.

Scheme 2 is specifically illustrated by Example 2, but is not limited to this particular example.

SCHEME III

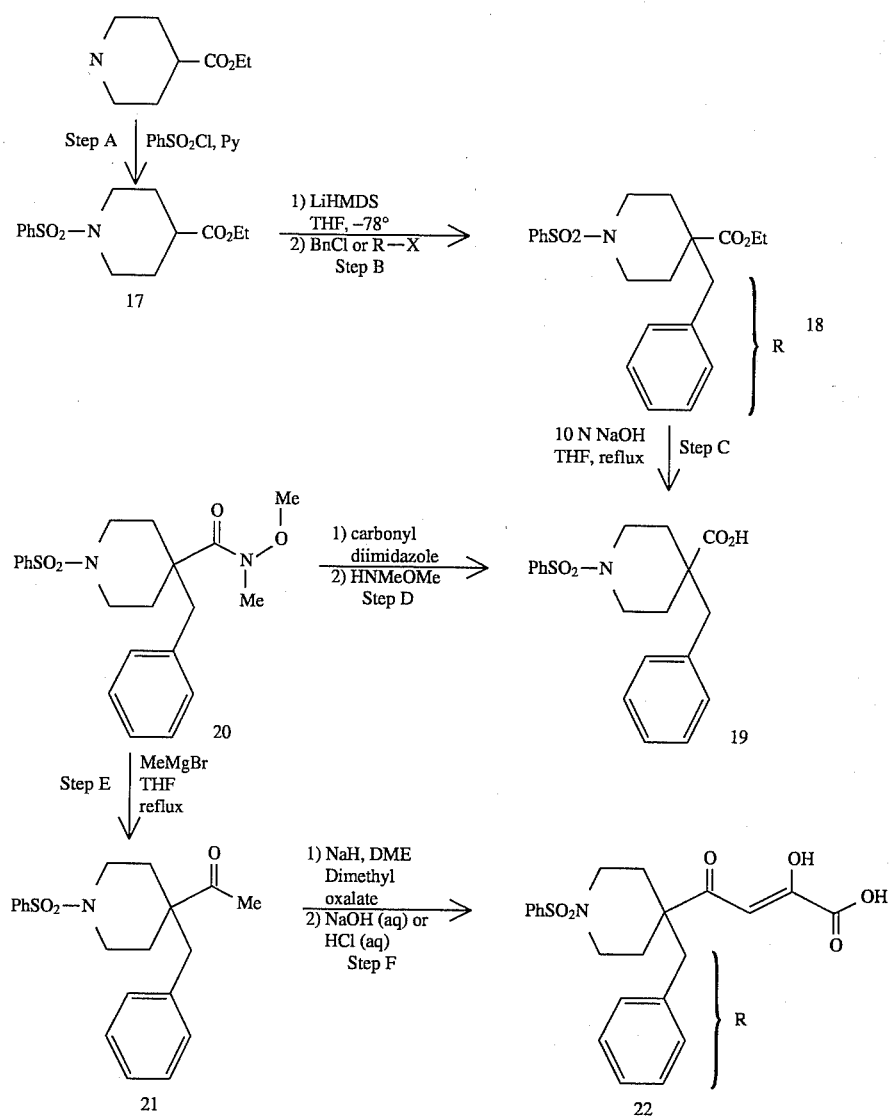

In Scheme III, 4-sulfonyl piperdine compounds of Formula I are readily prepared by variations of Scheme I. The sulfonyl substituent can be added first to give, for example, 17. This variation eliminates the steps of deprotection and alkylation of the piperidinyl nitrogen (Steps E and F of scheme I).

Scheme 3 is specifically illustrated by Example 3, but is not limited to this particular example.

The compounds invention include but are not limited to those of the following Tables 1, 2 and 3:

TABLE 1

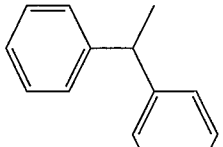

| Example | R | MP (°C.) |
|---|---|---|
| 2 | 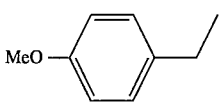 | 87–90 |
| 3 | 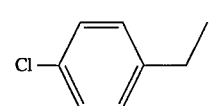 | 168–170 |
| 4 | 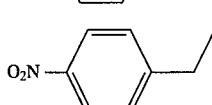 | 178–180 |
| 5 | 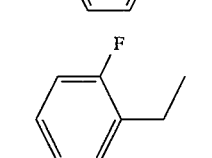 | 60–62 |
| 6 | 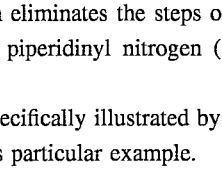 | 171–173 |// TABLE 1-continued

| Example | R | MP (°C.) |
|---|---|---|
| 7 | 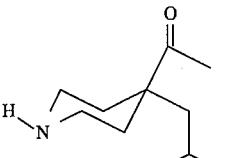 | 185–186 |
| 8 | 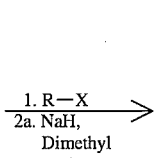 | 215–218 |
| 9 | 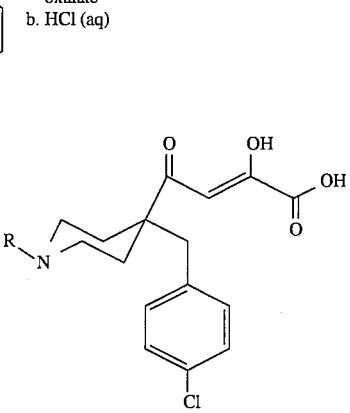 | 125–131 |
| 10 | 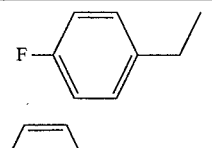 | 160–162 |
| 11 | 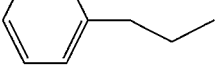 | 135–140 |
| 12 | 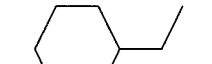 | 176–178 |
| 13 | 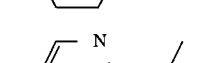 | 195–197 |
| 14 | 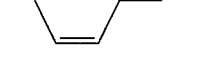 | 206–208 |
| 15 |  | 133–136 |
| 16 | 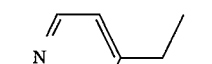 | 198–200 |

TABLE 1-continued
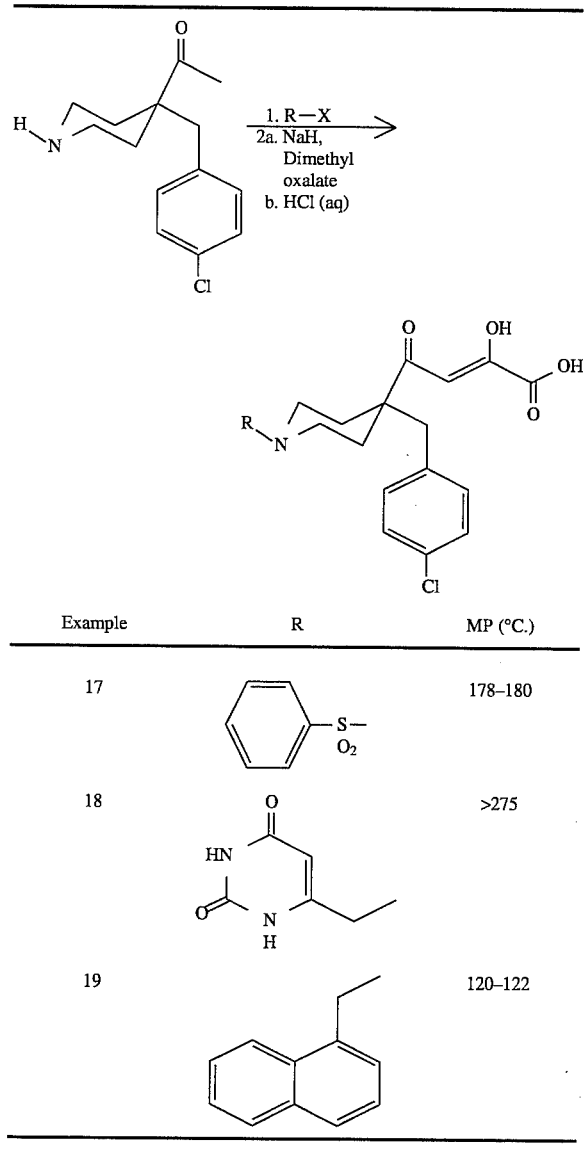
| Example | R | MP (°C.) |
|---|---|---|
| 17 | phenyl-SO₂– | 178–180 |
| 18 | ethyl-substituted uracil | >275 |
| 19 | 1-naphthylmethyl | 120–122 |
TABLE 2
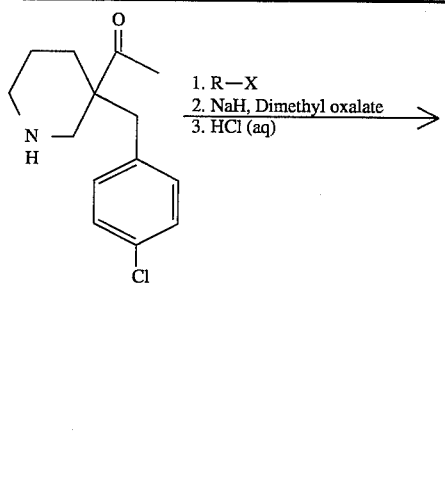
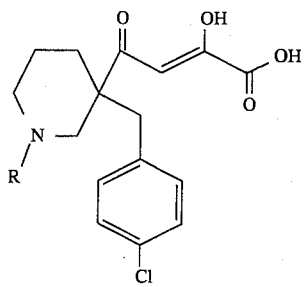
| Example | R | MP (°C.) |
|---|---|---|
| 21 | benzyl | 160–162 |
| 22 | H₃C(CH₂)₅CH₂– | 55–57 |
| 23 | 2-pyridylmethyl | 70–73 |
| 24 | 1-naphthylmethyl | 168–170 |
| 25 | (1-methylbenzimidazol-2-yl)methyl | 148–152 |
| 26 | 4-chlorobenzyl | 190–192 |
| 27 | 2-phenylethyl | 189–191 |
| 28 | 3-phenylpropyl | 184–187 |
| 29 | 1,3-dimethyluracil-ethyl | 117–119 |

Table 2 (continued)

Structure:

4-chlorobenzyl-substituted piperidine with N-R group, bearing a 4-oxo-2-hydroxy-but-2-enoic acid side chain.

| Example | R | MP (°C.) |
|---|---|---|
| 30 | phenyl-SO₂- | 74–77 |
| 31 | t-BuO-C(O)-CH₂- (tert-butoxycarbonylmethyl) | 154–155 |
| 32 | 4-MeO-C₆H₄-SO₂- | 120–125 |
| 33 | 4-F-C₆H₄-SO₂- | 70–73 |
| 34 | 4-HO₂C-C₆H₄-SO₂- | 209–211 |
| 35 | PhCH₂-SO₂- | 130–133 |
| 36 | n-Pr-SO₂- | 108–110 |
| 37 | t-Bu-C(O)- (pivaloyl) | 167–169 |
| 38 | Ph-C(O)- (benzoyl) | 212–215 |

TABLE 3

Structure: 4-R-substituted piperidine with N-SO₂-phenyl, bearing a 4-oxo-2-hydroxy-but-2-enoic acid side chain.

| Example | R | MP (°C.) |
|---|---|---|
| 40 | MeO-CH₂CH₂-CH₂- | 85–90 |
| 41 | 2-F-C₆H₄-CH₂CH₂- | 154–157 |
| 42 | 4-MeO-C₆H₄-CH₂CH₂- | 62–66 |
| 43 | Ph-CH₂CH₂CH₂CH₂- | 75–80 |
| 44 | 4-F-C₆H₄-CH₂CH₂- | 130–134 |
| 45 | 3-F-C₆H₄-CH₂CH₂- | 95–100 |
| 46 | isobutyl | 65–70 |
| 47 | 2-Cl-C₆H₄-CH₂CH₂- | 164–167 |
| 48 | 2-naphthyl-CH₂CH₂- | 114–120 |
| 49 | 4-biphenyl-CH₂CH₂- | 100–105 |
| 50 | 1-naphthyl-CH₂CH₂- | 114–120 |

TABLE 3-continued

[Structure: phenyl-S(O2)-N-piperidine with R substituent at 4-position, connected to C(=O)-CH=C(OH)-C(=O)OH]

| Example | R | MP (°C.) |
|---|---|---|
| 51 | 4-Cl-benzyl | 178–180 |
| 52 | 3-Cl-benzyl | 85–95 |
| 52 | 6-Cl-1,3-benzodioxol-5-ylmethyl | 120–130 |
| 54 | 3,4-difluorobenzyl | 172–174 |
| 55 | 3,4-difluorobenzyl | 98–100 |
| 56 | H₃C-(CH₂)₄- | 55–60 |
| 57 | 3,4-dichlorobenzyl | 89–91 |
| 58 | 2-phenylbenzyl | 95–97 |

The compounds of the present invention are useful in the inhibition of influenza virus cap-dependent endonuclease, and the prevention or treatment of infection by the influenza virus.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to influenza virus cap-dependent endonuclease, e.g., by competitive inhibition. Thus the compounds of this invention are commercial products to be sold for these purposes.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating influenza virus infection and influenza. The treatment involves administering to a patient in need of such treatment a pharmaceutical composition comprising a pharmaceutical carder and a therapeutically-effective mount of a compound of the present invention, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known an, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by influenza virus is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the influenza virus inhibitory compounds with one or more agents useful in the treatment of influenza. For example, the compounds of this invention may be effectively administered, whether at periods of pre-exposure and/or post-exposure, in combination with effective amounts of the influenza virus antivirals, immunomodulators, anti-infectives, or vaccines known to those of ordinary skill in the art.

EXAMPLE 1

4-[N-Benzy-4-(4-Chlorobenzyl)-piperidin-4-yl]-2,4-dioxobutanoic acid Hydrochloride

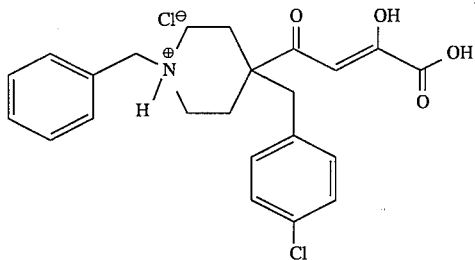

Step A: Ethyl-4-(4-Chlorobenzyl)-N-Boc-isonipecotate

A solution of ethyl-N-boc-isonipecotate (51.4 g, 0.2 mole) in tetrahydrofuran (1 L) at −78° C. was treated with a solution of lithium bis (trimethylsilyl)amide in tetrahydrofuran (220 mL of a 1M solution). The solution was stirred at −60° for 15 minutes at which time 4-chlorobenzyl chloride (33.8 g, 0.22 moles) was added and the reaction warmed to room temperature over 1.5 hours. The reaction was concentrated at reduced pressure to one quarter volume and then poured into saturated aqueous sodium bicarbonate (1 L) and extracted with ethyl acetate (2×800 mL). The combined organic extracts were dried over anhydrous magnesium sulfate, filtered, and concentrated at reduced pressure. The residue was chromatographed on silica gel with 30% ethyl acetate/hexane as eluent to give 61.3 g. $^1$H NMR CDCl$_3$ δ 7.22 (d, J=8.0 Hz, 2H), 6.97 (d, J=8.0 Hz, 2H), 4.10 (q, J=7 Hz, 2H), 3.90 (m, 2H), 2.8 (m, 2H), 2.8 (s, 2H), 2.05 (m, 2H), 1.44 (s, 9H), 1.40–1.30 (m, 2H), 1.15 (t, J=t Hz, 1H).

Step B: 4-(4-Chlorobenzyl)-N-boc-isonipecotic acid

The material thus obtained in Step A was dissolved in isopropyl alcohol (150 mL) and tetrahydrofuran (150 mL) and treated with 10N NaOH (250 mL). The mixture was heated at reflux for 48 hr. The reaction was cooled to room temperature and carefully neutralized by pouring over 1 L of crushed ice and adding 6N HCl until pH 3. The mixture was then extracted with ethyl acetate (3×500 mL). The combined organic extracts were dried over anhydrous magnesium sulfate, filtered, and concentrated at reduced pressure to give 16 g of the product. $^1$H NMR CDCl$_3$ δ 7.25 (d, J=8.5 Hz, 2H), 7.04 (d, J=8.5 Hz, 2H), 3.95 (m, 2H), 2.9 (m, 2H), 2.84 (s, 2H), 2.05 (m, 2H), 1.45 (s, 9H), 1.45–1.30 (m, 2H).

Step C: N-boc4-(4-Chlorobenzyl)-piperidine-4-carboxylic acid-(N,O-Dimethylmethylhydroxamide)

A solution of 4-(4-chlorobenzyl-N-boc-piperidine-4-carboxylic acid (52 g, 0.131 moles) in N,N-dimethylformamide (100 mL) at room temperature was treated with carbonyldiimidazole (25.7 g, 0.158 mol) and warmed to 60° C. for 15 minutes. N,O-dimethyl-hydroxylamine hydrochloride (30.8 g, 0.316 mole) was then added and the reaction stirred at 60° C. for 15 minutes. The reaction was then cooled to room temperature and aged for 1 hour. After stirring for 1 hour at room temperature the reaction was poured into saturated aqueous sodium bicarbonate and extracted with ethyl acetate (3×300 mL). The combined organic extracts were dried over anhydrous magnesium sulfate, filtered, and concentrated at reduced pressure to give 58 g of the title compound. $^1$H NMR CDCl$_3$ δ 7.20 (d, J=8.5 Hz, 2H), 6.98 (d, J=8.5 Hz, 2H), 3.93 (m, 2H), 3.70 (s, 3H), 3.19 (s, 3H), 2.98 (m, 2H), 2.96 (s, 2H), 2.21 (m, 2H), 1.45 (s, 9H), 1.45–1.30 (m, 2H).

Step D: N-boc-4-acetyl-4-(4-Chlorobenzyl)-piperidine

A solution of N-boc-4-(4-Chlorobenzyl)-piperidine-4-carboxylic acid-(N,O-Dimethylmethylhydroxamide) (48 g, 0.120 mol) in tetrahydrofuran (400 mL) was treated with a solution of methylmagnesium bromide (60 mL of a 3M solution in tetrahydrofuran, 0.18 mol) and heated to reflux for thirty minutes. The reaction was then cooled to room temperature, poured into saturated aqueous sodium bicarbonate (1.5 L) and extracted with ethyl acetate (3×500 mL). The combined organic extracts were dried over anhydrous magnesium sulfate, filtered, and concentrated at reduced pressure to give 25.2 g of the title compound. $^1$H NMR CDCl$_3$ δ 7.22 (d, J=8.5 Hz, 2H), 6.96 (d, J=8.5 Hz, 2H), 3.93 (m, 2H), 2.92 (m, 2H), 2.89 (s, 2H), 2.10 (s, 3H), 2.05 (m, 2H), 1.45 (s, 9H), 1.50–1.30 (m, 2H).

Step E: 4-Acetyl-4-(4-Chlorobenzyl)-piperidine hydrochloride

HCl gas was bubbled into a solution of N-boc-4-acetyl-4-(4-chlorobenzyl)-piperidine (25 g, 0.071 mol) in ethyl acetate (300 mL) for 15 minutes. The reaction was concentrated at reduced pressure and the solid collected to give 20.3 g of product. $^1$H NMR d6 DMSO δ 9.1 (br s, 1H), 8.8 (br s, 1H), 7.30 (d, J=8.0 Hz, 2H), 6.96 (d, J=8.0 Hz, 2H), 3.13 (m, 2H), 2.92 (s, 2H), 2.65 (m, 2H), 2.13 (s, 3H), 2.05 (m, 2H), 1.70 (m, 2H).

Step F: N-Benzyl-4-Acetyl4-(4-Chlorobenzyl)-piperidine

A suspension of 4-Acetyl-4-(4-chlorobenzyl)-piperidine hydrochloride (0.600 g, 2.09 mmol) in acetonitrile (20 mL) was treated with solid sodium bicarbonate (200 mg, xs) and benzyl chloride (292 mg, 2.3 mol) and heated to reflux for 3 hours. The reaction was then cooled to room temperature, poured into saturated aqueous sodium bicarbonate (200 mL) and extracted with ethyl acetate (3×100 mL). The combined extracts were dried over anhydrous magnesium sulfate, filtered, and concentrated at reduced pressure. The residue was chromatographed on silica gel eluting with 2% Methanol/chloroform to give 706 mg of the title compound. $^1$H NMR CDCl$_3$ δ 7.25 (m, 5H), 7.22 (d, J=8.5 Hz, 2H), 6.96 (d, J=8.5 Hz, 2H), 3.45 (s, 2H), 2.78 (s 2H), 2.76 (m, 2H), 2.20–2.0 (m, 4H), 2.06 (s, 3H), 1.75–1.50 (m, 2H).

Step G: 4-[N-Benzyl-4-(4-Chlorobenzyl)-piperidin-4-yl]-2,4-dioxo-butanoic acid Hydrochloride A solution of N-Benzyl-4-Acetyl-4-(4-Chlorobenzyl)-piperidine (600 mg, 1.75 mmol) and dimethyl oxalate (310 mg, 2.63 mmol) in dimethoxyethane (20 mL) was treated with sodium hydride (105 mg of a 60% dispersion in mineral oil, 2.63 mmol) and heated to reflux for 3 hours. The reaction was then cooled to room temperature, poured into 1 N aqueous HCl (200 mL) and extracted with ethyl ether (1×50 mL). The ether extract was discarded. The pH of the aqueous phase was adjusted to pH 8 and extracted with ethyl acetate (3×200 mL). The combined extracts were dried over anhydrous magnesium sulfate, filtered, and concentrated at reduced pressure. The crude ester thus obtained was dissolved in THF (5 mL) and 3 N HCl (20 mL) and heated to reflux for 1 hour. The reaction was then cooled to room temperature, and concentrated at reduced pressure. The residue was triturated with tetrahydrofuran and the solid collected by filtration and crystallized from isopropanol to give 200 mg of the title compound. mp. 189°–181° C.

Elemental analysis for $C_{23}H_{24}ClNO_4 \cdot HCl \cdot IPA$
Calculated: C, 60.64; H, 6.56; N, 2.72
Found: C, 60.61; H, 6.46; N, 2.65

EXAMPLE 2

4-[N-Benzyl-3-(4-Chlorobenzyl)-piperidin-3-yl]-2,4-dioxobutanoic acid Hydrochloride

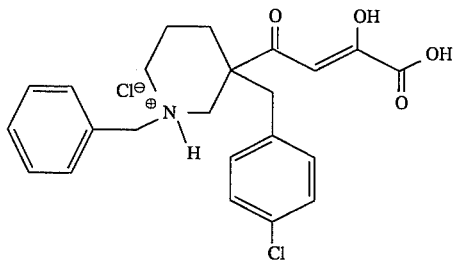

Step A: Ethyl-3-(4-chlorobenzyl)-N-Boc-piperidin-3-carboxylate

A solution of ethyl-N-boc-nipecotate (45 g, 0.18 mole) in tetrahydrofuran (200 mL) at −40° C. was treated with a solution of lithium bis (trimethylsilyl)amide in tetrahydrofuran (320 mL of a 1M solution). The solution was stirred at −40° for 15 minutes at which time 4-Chlorobenzyl chloride (34.59 g, 0.215 moles) was added and the reaction warmed to room temperature over 1.5 hours. The reaction was poured into saturated aqueous sodium bicarbonate (1 L) and extracted with ethyl acetate (3×500 mL). The combined organic extracts were dried over anhydrous magnesium sulfate, filtered, and concentrated at reduced pressure. The residue was chromatographed on silica gel with 30% ethyl acetate/hexane as eluent to give 36.5 g. $^1$H NMR CDCl$_3$ δ 7.22 (d, J=8.5 Hz, 2H), 7.05 (d, J=8.5 Hz, 2H), 4.1–3.8 (m, 3H), 3.55 (m, 1H), 3.15 (m, 1H), 2.9 (d, J=13 Hz, 1H), 2.7 (d, J=13 Hz, 1H), 2.00 (m, 1H), 1.80–1.40 (m, 3H), 1.44 (s, 9H), 1.15 (t, J=7 Hz, 3H).

Step B: N-boc-3-(4-chlorobenzyl)piperidin-3-carboxylic acid

A suspension of Ethyl-3-(4-chlorobenzyl)-N-Boc-piperidin-3-caroxylate (36.4 g, 0.105 mol) in isopropyl alcohol (300 mL) was treated with 10N NaOH (300 mL). The mixture was heated at reflux for 48 hours. The reaction was cooled to room temperature and carefully neutralized by pouting over 1 L of crashed ice and adding 6 N HCl until pH 3. The mixture was then extracted with ethyl acetate (3×500 mL). The combined organic extracts were dried over anhydrous magnesium sulfate, filtered, and concentrated at reduced pressure to give 31 g of the product. $^1$H NMR CDCl$_3$ δ 10.18 (br s), 7.26 (d, J=8.5 Hz, 2H), 7.04 (d, J=8.5 Hz, 2H), 3.95 (m, 1H), 3.6 (m, 1H), 3.2 (m, 2H), 2.90 (d, J=12 Hz, 1H), 2.78 (d, J=12 Hz, 1H), 2.00 (m, 1H), 1.75–1.30 (m, 3H), 1.44 (s, 9H).

Step.C: N-boc-3-(4-Chlorobenzyl)-piperidine-3-carboxylic acid-(N,O-Dimethylmethylhydroxamide)

A solution of 3-(4-chlorobenzyl)-N-boc-nipecotic acid (23 g, 0.064 moles) in methylene chloride (500 mL) at room temperature was treated with DMF (2 mL) and oxalyl chloride (8.5 mL), and stirred at room temperature for 1 hr. The reaction was then concentrated at reduced pressure and the crude acid chloride redissolved in methylene chloride (500 mL). A suspension of N,O-dimethylhydroxylamine hydrochloride (12.68 g, 0.129 mole) in pyridine (50 mL) was then added and the reaction stirred at room temperature for one hour. The reaction was then poured into saturated aqueous sodium bicarbonate (1) and extracted with ethyl acetate (3×300 mL). The combined extracts were dried over anhydrous magnesium sulfate, filtered, and concentrated at reduced pressure to give 26.1 g of the title compound. $^1$H NMR CDCl$_3$ δ 7.15 (d, J=8.5 Hz, 2H), 7.04 (d, J=8.5 Hz, 2H), 3.95–3.6 (m, 2H), 3.75 (br s, 3H), 3.2–3.0 (m, 2H), 3.0 (s, 3H), 2.98–2.6 (m, 2H), 2.00–1.5 (m, 4H), 1.40 (s, 9H).

Step D: N-Boc-3-acetyl-3-(4-Chlorobenzyl)-piperidine

A solution of N-boc-3-(4-Chlorobenzyl)-piperidine-3-carboxylic acid-(N,O-Dimethylmethylhydroxamide) (25.59 g, 0.064 mol) in tetrahydrofuran (200 mL) was treated with a solution of methylmagnesium bromide (64.5 mL of a 3M solution in tetrahydrofuran, 0.194 mol) and heated to reflux for thirty minutes. The reaction was then cooled to room temperature poured into saturated aqueous sodium bicarbonate (1 L) and extracted with ethyl acetate (3×500 mL). The combined extracts were dried over anhydrous magnesium sulfate, filtered, and concentrated at reduced pressure to give 12.2 g of the title compound. $^1$H NMR CDCl$_3$ δ 7.25 (d,=8.5 Hz, 2H), 7.00 (d,=8.5 Hz, 2H), 4.3 (m, 1H), 3.7 (m, 2H), 3.3–2.6 (m, 5H), 2.10–2.00 (m, 1H), 2.05 (s, 3H), 1.70–1.20 (m, 3H), 1.45 (s, 9H).

Step E: 3-Acetyl-3-(4-Chlorobenzyl),piperidine hydrochloride

HCl gas was bubbled into a solution of N-boc-3-acetyl-3-(4-Chlorobenzyl)-piperidine (20.46 g, 0.058 mol) in ethyl acetate (300 mL) for 15 minutes. The reaction was concentrated at reduced pressure and the solid collected to give 16 g of product. $^1$H NMR d6 DMSO δ 9.1 (br s, 1H), 8.8 (br s, 1H), 7.30 (d,=8.0 Hz, 2H), 6.96 (d,=8.0 Hz, 2H), 3.13 (m, 2H), 2.92 (s, 2H), 2.65 (m, 2H), 2.13 (s, 3H), 2.05 (m, 2H), 1.70 (m, 2H).

Step F: N-Benzyl-3-acetyl-3-(4-chlorobenzyl)-piperidine

A suspension of 3-Acetyl-3-(4-Chlorobenzyl)-piperidine hydrochloride (0.7 g, 2.43 mmol) in acetonitrile (20 mL) was treated with solid sodium bicarbonate (200 mg, 4.8 mmoles) and benzyl chloride (369 mg, 2.9 mol) and heated to reflux for 2 hours. The reaction was then cooled to room temperature, poured into saturated aqueous sodium bicarbonate (200 mL) and extracted with ethyl acetate (3×100 mL). The combined organic extracts were dried over anhydrous magnesium sulfate, filtered, and concentrated at reduced pressure. The residue was chromatographed on silica gel eluting with 2% methanol/chloroform to give 492 mg of the title compound. $^1$H NMR CDCl$_3$ δ 7.40–7.25 (m, 5H), 7.22 (d,=8.5 Hz, 2H), 6.90 (d,=8.5 Hz, 2H), 3.45 (m, 2H), 3.00 (m, 1H), 2.80–2.50 (m, 3H), 2.20–1.90 (m, 4H), 2.00 (s, 3H), 1.60–1.50 (m, 2H), 1.30–1.10 (m, 1H).

Step G: 4-[N-Benzyl-3-(4-chlorobenzyl)-piperidin-3-yl]-2,4-dioxobutanoic acid Hydrochloride A solution of N-Benzyl-3-acetyl-3-(4-chlorobenzyl)-piperidine (492 mg, 1.44 mmol) and dimethyl oxalate (201 mg, 1.7 mmol) in dimethoxyethane (20 mL) was treated with sodium hydride (140 mg of a 60% dispersion in mineral oil, 3.4 mmol) and heated to reflux for 5 hours. The reaction was then cooled to room temperature, poured into saturated sodium bicarbonate (100 mL) and extracted with ethyl acetate (3×100 mL). The combined extracts were dried over anhydrous magnesium sulfate, filtered, and concentrated at reduced pressure. The crude ester thus obtained was purified by chromato-graphy on silica gel eluting with 10% methanol/chloroform. The material thus obtained was dissolved in tetrahydrofuran (5 mL) and 3N HCl (20 mL) and heated to reflux for 1 hour. The reaction was then cooled to room temperature, and concentrated at reduced pressure. The residue was triturated with tetrahydrofuran and the solid collected by filtration and crystallized from isopropanol to give 35 mg of the title compound. mp. 160°–165° C.

Elemental analysis for $C_{23}H_{24}ClNO_4 \cdot HCl$
Calculated: C, 61.34; H, 5.60; N, 3.11
Found: C, 61.34; H, 5.87; N, 3.39

EXAMPLE 3

4-[N-Benzenesulfonyl-4-(benzyl)-piperidin-4-yl]-2,4-dioxobutanoic acid

Step A: Ethy-N-benzenesulfonyl-piperidine-4-carboxylate

A solution of ethyl isonipecotate (15.7 g, 0.1 mol) in methylene chloride (100 mL) at 0° C. was treated with pyridine (10 mL) and then benzenesulfonyl chloride (17.6 g, 0.1 mol). The reaction was warmed to room temperature and stirred at room temperature for 2 hours. The reaction was then poured into 1N HCl (1 L) and extracted with ethyl acetate (2×500 mL). The combined extracts were dried over anhydrous magnesium sulfate, filtered, and concentrated at reduced pressure. The solid was recrystallized from ethyl acetate to give 17 g of product. $^1$H NMR CDCl$_3$ δ 7.78 (d, J=6.0 Hz, 2H), 7.65–7.50 (m, 3H), 4.1 (q, J=6.8 Hz, 2H), 3.62 (m, 2H), 2.50 (dt, J=3, 11.5 Hz, 2H), 2.25 (m, 1H), 2.03–1.90 (m, 2H), 1.85–1.75 (m, 2H), 1.33 (t, J=6.8 Hz, 3H).

Step B: Ethyl-N-Benzenesulfonyl-4-(benzyl)-piperidine-4-carboxylate

A solution of ethyl-N-benzenesulfonyl-isonipecotate (5 g, 0.016 mole) in tetrahydrofuran (1 L) at −78° C. was treated with a solution of Lithium bis (trimethylsilyl)amide in tetrahydrofuran (18.5 mL of a 1M solution). The solution was stirred at −60° for 15 minutes at which time benzyl bromide (3.15 g, 0.016 moles) was added and the reaction warmed to room temperature over 1.5 hours. The reaction was concentrated at reduced pressure to @ one quarter volume and then poured into saturated aqueous sodium bicarbonate (1 L) and extracted with ethyl acetate (2×800 mL). The combined extracts were dried over anhydrous magnesium sulfate, filtered, and concentrated at reduced pressure. The residue was chromatographed on silica gel with 30% ethyl acetate/hexane as eluent to give 5.1 g. $^1$H NMR CDCl$_3$ δ 7.7 (d,=8.5 Hz, 2H), 7.6–7.4 (m, 3H), 7.3–7.2 (m, 3H), 7.1–7.0 (m, 2H), 3.98 (q, J=7 Hz, 2H), 3.65 (m, 2H), 2.78 (s, 2H), 2.35 (dt, J=2.5, 12 Hz, 2H), 2.19 (d, J=12 Hz, 2H), 1.61 (dt, J=4.5, 12 Hz, 2H).

Step C: N-Benzenesulfonyl-4-(benzyl)-piperidine-4-carboxylic acid

The material thus obtained was dissolved in isopropyl alcohol tetrahydrofuran (150 mL) and treated with 6N NaOH (250 mL). The mixture was heated to reflux for 48 hours. The reaction was cooled to room temperature and carefully neutralized by pouring over 1 L of crashed ice and adding 6N HCl until pH 3. The mixture was then extracted with ethyl acetate (3×500 mL). The combined extracts were dried over anhydrous magnesium sulfate, filtered, and concentrated at reduced pressure to give 4.1 g of the product. $^1$H NMR d6 DMSO δ 7.70–7.60 (m, 5H), 7.30–7.15 (m, 3H), 7.06 (m, 2H), 3.55 (m, 2H), 2.72 (s, 2H), 2.15 (app t, J=12 Hz, 2H), 1.98 (app d, J=12 Hz, 2H), 1.50 (app dt, J=2,12 Hz, 2H).

Step D: N-Benzenesulfonyl-4-(benzyl)-piperidine-4-carboxylic acid-(N,O-Dimethylmethylhydroxamide)

A solution of N-benzenesulfonyl-4-(4-chlorobenzyl)-piperidine-4-carboxylic acid (52 g, 0.131 moles) in DMF (100 mL) at room temperature was treated with carbonyldiimidazole (25.7 g, 0.158 mol mL) and warmed to 60° C. for 15 minutes. N,O-dimethylhydroxylamine hydrochloride (30.8 g, 0.316 mole) was then added and the reaction stirred at 60° C. for 15 minutes. The reaction was then cooled to room temperature and aged for 1 hour. After stirring for 1 hour at room temperature the reaction was poured into saturated aqueous sodium bicarbonate and extracted with ethyl acetate (3×300 mL). The combined extracts were dried over anhydrous magnesium sulfate, filtered, and concentrated at reduced pressure to give 58 g of the title compound. $^1$H NMR CDCl$_3$ δ 7.20 (d,=8.5 Hz, 2H), 6.98 (d,=8.5 Hz, 2H), 3.93 (m, 2H), 3.70 (s, 3H), 3.19 (s, 3H), 2.98 (m, 2H), 2.96 (s, 2H), 2.21 (m, 2H), 1.45 (s, 9H), 1.45–1.30 (m, 2H).

Step E: N-Benzenesulfonyl-4-acetyl-4-(benzyl)-piperidine

A solution of N-Benzenesulfonyl-4-(4-chlorobenzyl)-piperidine-4-carboxylic acid-(N,O-Dimethylmethylhydroxamide) (48 g, 0.120 mol) in tetrahydrofuran (400 mL) was treated with a solution of methylmagnesium bromide (60 mL of a 3N solution in tetra-hydrofuran, 0.18 mol) and heated to reflux for thirty minutes. The reaction was then cooled to room temperature, poured into saturated aqueous sodium bicarbonate (1.5 L) and extracted with ethyl acetate (3×500 mL). The combined extracts were dried over anhydrous magnesium sulfate, filtered, and concentrated at reduced pressure to give 25.2 g of the title compound. $^1$H NMR CDCl$_3$ δ 7.22 (d,=8.5 Hz, 2H), 6.96 (d,=8.5 Hz, 2H), 3.93 (m, 2H), 2.92 (m, 2H), 2.89 (s, 2H), 2.10 (s, 3H), 2.05 (m, 2H), 1.45 (s, 9H), 1.50–1.30 (m, 2H).

Step F: 4-[N-Benzenesulfonyl-4-(benzyl)-piperidin-4-yl]-2,4-dioxobutanoic acid

A solution of N-Benzyl-4-acetyl-4-(4-chlorobenzyl)-piperidine (600 mg, 1.75 mmol) and dimethyl oxalate (310 mg, 2.63 mmoles) in dimethoxyethane (20 mL) was treated with sodium hydride (105 mg of a 60% dispersion in mineral oil, 2.63 mmoles) and heated to reflux for 3 hours. The reaction was then cooled to room temperature, poured into 1N aqueous HCl (200 mL) and extracted with ethyl ether (1×50 mL). The ether extract was discarded. The pH of the aqueous phase was adjusted to pH 8 and extracted with ethyl acetate (3×200 mL). The combined extracts were dried over anhydrous magnesium sulfate, filtered, and concentrated at reduced pressure. The crude ester thus obtained was dissolved in tetrahydrofuran (5 mL) and 3N NaOH (20 mL) and stirred at room temperature for 1 hour. The reaction was then cooled to room temperature, and concentrated at reduced pressure. The residue was triturated with THF and the solid collected by filtration and crystallized from isopropanol to give 200 mg of the title compound. mp. 189°–181° C. Elemental analysis for $C_{23}H_{24}ClNO_4.HCl.IPA$
Calculated: C, 60.64; H, 6.56; N, 2.72
Found: C, 60.61; H, 6.46; N, 2.65

EXAMPLE 4

SUMMARY BIOLOGICAL DATA FOR DIOXOBUTANOIC ACIDS

I. IDENTIFICATION OF IN VITRO INHIBITORY ACTIVITY

The dioxobutanoic acid inhibitors were identified in an in vitro screen which was established for the identification of inhibitors of influenza primary transcription (FLUTIN) in our laboratory. The assay consisted of detergent-disrupted influenza virions as the enzyme source to which was added a capped and methylated primer, alfalfa mosaic virus (ALMV) RNA segment 4, and ribonucleotide triphosphates, one of which was radiolabeled to measure the incorporation into RNA by TCA precipitation. The inhibitory compounds had IC$_{50}$s ranging from 0.2–29.0 μM in influenza transcription.

II. SPECIFIC PROTOCOLS a. ALMV-primed flu transcription-Samples or DMSO were incubated for 60 min at 31° C. in a final reaction mixture containing 20 ng/µl flu APR8 virus; 2 ng/µl ALMV capped primer (880 nt); 2 ng/µl tRNA; 100 µM ATP, 50 µM C and GTP, 1 µM UTP and 0.3 µM $^{35}$S-UTP in 100 mM Tris-HCl, pH 7.8/0.25% Triton-N-100/100 mM KCl/5 mM MgCl$_2$/1 mM DTT. Reaction product was quantitated by TCA precipitation on glass fiber filters, followed by liquid scintillation counting.

b. ApG-primed flu transcription-Samples or DMSO were incubated in a fmal reaction mixture as in a. above, with 200 µM ApG replacing ALMV primer.

c. VSV transcription-Samples or DMSO were incubated for 60 min at 31° C. in a final reaction mixture containing 20 ng/µl of VSV; 2 ng/µl of tRNA; 100 µM ATP; 50 µM C and GTP; 1 µM UTP and 0.3 µM $^{35}$S-UTP; in 50 mM Tris-HCl, pH 8.0/100 mM NaCl/4 mM DTT/0.05% Triton-N-100/5 mM MgCl$_2$. Reaction product was quantitated by TCA precipitation onto glass fiber filters, followed by liquid scintillation counting.

d. Hela RNA polymerase II-Compounds or DMSO were incubated in a run-off transcription assay using Hela RNA polymerase II in Hela extract with 50 ng/µl of pD5 template (Adeno major late promoter) in a final reaction containing 500 µM A,C,GTP and 0.5 µM $^{32}$P-UTP in 15 mM Tris-HCl, pH 7.9/7.0 mM MGCl$_2$/32 mM (NH$_4$)$_2$SO$_4$/0.2 mM EDTA/1.3 mM DTT for 60 min at 30° C. Following ethanol precipitation, reaction products were electrophoresed on 8% polyacrylamide gels containing 7M urea.

e. 13, 22, 70 nt-primed flu transcription assays-Samples or DMSO were tested in transcription as in (a) above with purified polymerase cores at a concentration of 2 ng/µl replacing APR8 virus and primed with 10 nM synthetic ALMV capped primers (13, 22, 70 nt) replacing ALMV primer (880 nt) for 40 min. Reaction was quantitated by TCA precipitation.

f. Flu Cleavage-Samples or DMSO were tested in a final reaction mixture containing 2.5 ng/µl of purified polymerase cores; 1 ng/µl of tRNA; 0.5 µ/µl of RNasin; and 5.5 nM of $^{32}$P-radiolabeled ALMV in 50 mM Tris-HCl, pH 7.8/100 mM KCl/5 mM MgCl$_2$/1 mM DTT for 30 min. The reaction was stopped by addition of an equal volume of 95% formamide buffer and then electrophoresed on a 12% polyacrylamide gels containing 7M urea, followed by quantitation by direct radioanalytic imaging.

g. RNase Assays-Compound or sample was tested in various RNase assays as follows. Radiolabeled ALMV substrate as in (f), was incubated at 5.5 nM with 0.02 units/µl of RNase T1 or 0.04 units/µl of RNase U2 in 10 mM NaCitrate, pH 5.0/0.5 mM EDTA/7M urea at 56° C. for 20 min and reaction products were electrophoresed on 12% polyacrylamide gels containing 7M urea as in (f). RNase A at 4 ng/µl was incubated with 5.5 nM radiolabeled ALMV substrate in 10 mM NaCitrate, pH 3.5/0.5 mM EDTA/7M urea at 30° C. for 20 min. and reaction products were electrophoresed as above.

III. DATA FOR COMPOUND A

TABLE 3

| BIOCHEMICAL SPECIFICITY OF COMPOUND A | |
|---|---|
| Polymerase | IC$_{50}$ (µM) |
| ALMV (880 nt)-primed flu transcription | 1.1 |
| ApG-primed flu transcription | >1000.0 |
| VSV transcription | >500.0 |
| HIV Reverse Transcriptase | >300.0 |
| T7 Phage RNA Polymerase | >100.0 |
| Hela RNA Polymerase II | >500.0 |
| Hela DNA Polymerase-a | >100.0 |
| Nuclease | IC$_{50}$ (µM) |
| HIV RNase H | 100.0 |
| U. sphaerogena RNase U2 | >200.0 |
| A. orzae RNase T1 | >200.0 |
| Bovine pancreatic RNase A | >200.0 |
| EcoRI Restriction Endonuclease | >500.0 |
| Influenza Endonuclease | 1.8 |

Compound A was tested in biochemical assays at concentrations in the range of 1.0–500 µM as described in materials and methods.

TABLE 4

| INHIBITION OF INFLUENZA A AND B VIRUS TRANSCRIPTION WITH COMPOUND A | |
|---|---|
| Virus Strain | IC$_{50}$ (µM) |
| A/PR/8/34 (H1N1) | 1.10 |
| A/Japan/305/57 (H2N2) | 0.25 |
| A/Port Chalmers/1/73 (H3N2) | 0.50 |
| A/Hong Kong/8/68 (H3N2) | 0.62 |
| B/Hong Kong/5/72 | 0.85 |

Compound A was tested in in vitro transcription with various influenza viruses primed with cap1 ALMV as described in material and methods.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. Pharmaceutical composition, for use in the treatment of influenza, in the prevention of infection by influenza virus, or in the inhibition of influenza cap-dependent endonuclease, comprising a pharmaceutically acceptable carrier and an effective amount of a compound of the formula

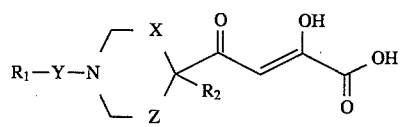

or pharmaceutically acceptable salt, hydrate or crystal form thereof, wherein:

X is —CH$_2$—, CH$_2$—CH$_2$—, or a bond;

Z is —CH$_2$—, CH$_2$—CH$_2$—, or a bond;

Y is —CH$_2$—, CO, SO$_2$—, or a bond;

R$_1$ and R$_2$ are independently selected from the following:

branched or unbranched C$_{1-6}$ alkyl-, C$_{1-6}$ alkyloxy-, —N—C$_{1-6}$ alkyl-, C$_{3-8}$ cycloalkyl-, phenyl, naphthyl, pyridyl, furanyl, thienyl, or quinolinyl, any of which may be substituted once or twice with $C_{1-5}$ alkyl, $C_{3-8}$ cycloalkyl, phenyl, quinolinyl, pyridyl, furanyl, thienyl, $C_{1-6}$-alkoxy, Br, F, or Cl.

2. Pharmaceutical composition, for use in the treatment of influenza, in the prevention of infection by influenza virus, or in the inhibition of influenza cap-dependent endonuclease, comprising a pharmaceutically acceptable carrier and an effective amount of a compound of the formula

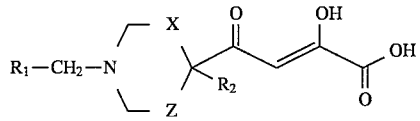

or pharmaceutically acceptable salt, hydrate or crystal form thereof,
wherein:
X is —$CH_2$—, $CH_2$—$CH_2$—, or a bond;
Z is —$CH_2$—, $CH_2$—$CH_2$—, or a bond;
$R_1$ is
  (i) phenyl, unsubstituted or substituted with halo; or
  (ii) cyclohexyl;
$R_2$ is
  (i) H or
  (ii) benzyl, unsubstituted or substituted with halo.

3. Pharmaceutical composition, for use in the treatment of influenza, in the prevention of infection by influenza virus, or in the inhibition of influenza cap-dependent endonuclease, comprising a pharmaceutically acceptable carrier and an effective amount of a compound of the structure

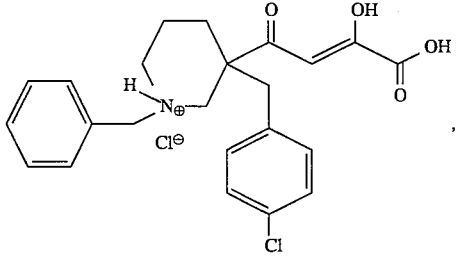

named
4-[N-benzyl-3-(4-chlorobenzyl)piperidin-3-yl]2,4-dioxobutanoic acid hydrochloride, or pharmaceutically acceptable salt, hydrate or ester thereof.

4. Pharmaceutical composition, for use in the treatment of influenza, in the prevention of infection by influenza virus, or in the inhibition of influenza cap-dependent endonuclease, comprising a pharmaceutically acceptable carrier and an effective amount of a compound of the structure

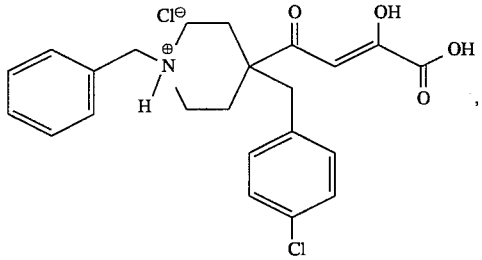

named
4-[N-benzyl-4-(p-chlorobenzyl)piperidin-4-yl]2,4-dioxobutanoic acid hydrochloride, or pharmaceutically acceptable salt, hydrate or ester thereof.

5. Pharmaceutical composition, for use in the treatment of influenza, in the prevention of infection by influenza, or in the inhibition of influenza cap-dependent endonuclease, comprising a pharmaceutically acceptable carrier and an effective amount of a compound of the structure

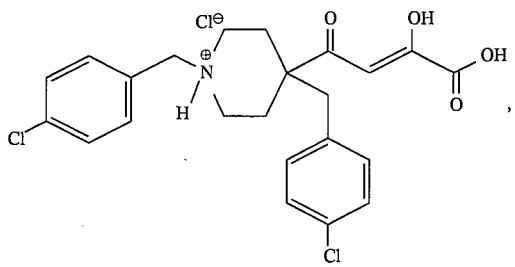

named
4-N-(p-chlorobenzyl)-4-(p-chlorobenzyl)piperidin-4-yl]
  2,4-dioxobutanoic acid hydrochloride, or pharmaceutically acceptable salt, hydrate or ester thereof.

6. Pharmaceutical composition, for use in the treatment of influenza, in the prevention of infection by influenza virus, or in the inhibition of influenza cap-dependent endonuclease, comprising a pharmaceutically acceptable carrier and an effective amount of a compound of the structure

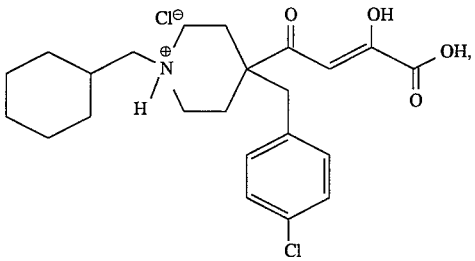

named
4-[1-cyclohexylmethyl-4-(p-chlorobenzyl)piperidin-4-yl]2,4-dioxobutanoic acid hydrochloride, or pharmaceutically acceptable salt, hydrate or ester thereof.

7. A method of heating influenza, comprising administering to a mammal in need of such treatment, an effective amount of a compound of the formula

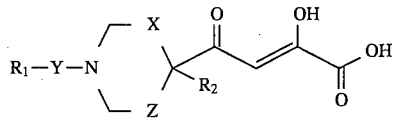

or pharmaceutically acceptable salt, hydrate or crystal form thereof,
wherein:
X is —$CH_2$—, $CH_2$—$CH_2$—, or a bond;
Z is —$CH_2$—, $CH_2$—$CH_2$—, or a bond;
Y is —$CH_2$—, CO, $SO_2$—, or a bond;
$R_1$ and $R_2$ are independently selected from the following:
  branched or unbranched $C_{1-6}$ alkyl-, $C_{1-6}$ alkyloxy-, —N—$C_{1-6}$ alkyl-, $C_{3-8}$ cycloalkyl-, phenyl, naphthyl, pyridyl, furanyl, thienyl, or quinolinyl, any of which may be substituted once or twice with $C_{1-5}$ alkyl, $C_{3-8}$ cycloalkyl, phenyl, quinolinyl, pyridyl, furanyl, thienyl, $C_{1-6}$-alkoxy, Br, F, or Cl.

8. A method of treating influenza, comprising administering to a mammal in need of such treatment, an effective amount of a compound of the formula

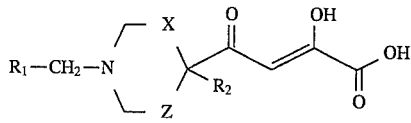

or pharmaceutically acceptable salt, hydrate or crystal form thereof,
wherein:

X is —CH$_2$—, CH$_2$—CH$_2$—, or a bond;

Z is —CH$_2$—, CH$_2$—CH$_2$—, or a bond;

R$_1$ is
   (i) phenyl, unsubstituted or substituted with halo; or
   (ii) cyclohexyl;

R$_2$ is
   (i) H or
   (ii) benzyl, unsubstituted or substituted with halo.

9. A method of treating influenza, comprising administering to a mammal in need of such treatment, an effective amount of a compound of the structure

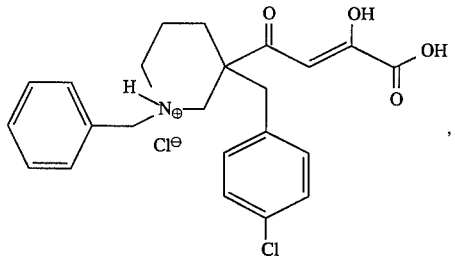

named
4-[N-benzyl-3-(4-chlorobenzyl)piperidin-3-yl]2,4-dioxobutanoic acid hydrochloride, or pharmaceutically acceptable salt, hydrate or ester thereof.

10. A method of treating influenza, comprising administering to a mammal in need of such treatment, an effective amount of a compound of the structure

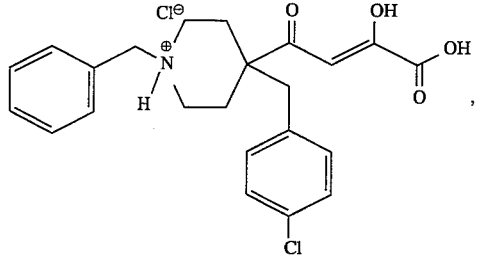

named
4-[N-benzyl-4-(p-chlorobenzyl)piperidin-4-yl]2,4-dioxobutanoic acid hydrochloride, or pharmaceutically acceptable salt, hydrate or ester thereof.

11. A method of treating influenza, comprising administering to a mammal in need of such treatment, an effective amount of a compound of the structure

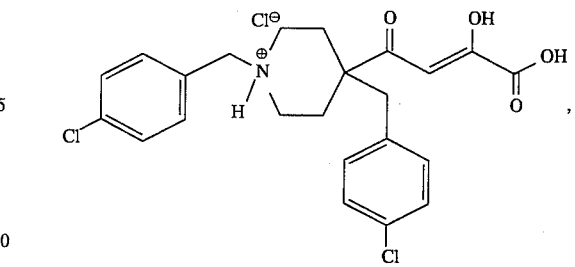

named
4-N-(p-chlorobenzyl)-4-(p-chlorobenzyl)piperidin-4-yl]
   2,4-dioxobutanoic acid hydrochloride, or pharmaceutically acceptable salt, hydrate or ester thereof.

12. A method of treating influenza, comprising administering to a mammal in need of such treatment, an effective amount of a compound of the structure

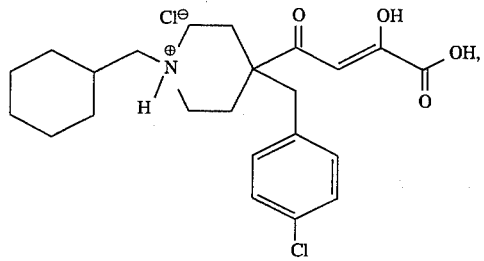

named
4-[1-cyclohexylmethyl-4-(p-chlorobenzyl)piperidin-4-yl]
   2,4-dioxobutanoic acid hydrochloride, or pharmaceutically acceptable salt, hydrate or ester thereof.

13. A method of preventing infection by influenza virus, comprising administering to a mammal in need of such treatment, an effective amount of the formula

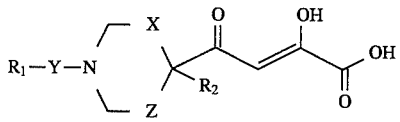

or pharmaceutically acceptable salt, hydrate or crystal form thereof,
wherein:

X is —CH$_2$—, CH$_2$—CH$_2$—, or a bond;

Z is —CH$_2$—, CH$_2$—CH$_2$—, or a bond;

Y is —CH$_2$—, CO, SO$_2$—, or a bond;

R$_1$ and R$_2$ are independently selected from the following:
   branched or unbranched C$_{1-6}$ alkyl-, C$_{1-6}$ alkyloxy-, —N—C$_{1-6}$ alkyl-, C$_{3-8}$ cycloalkyl-, phenyl, naphthyl, pyridyl, furanyl, thienyl, or quinolinyl, any of which may be substituted once or twice with C$_{1-5}$ alkyl, C$_{3-8}$ cycloalkyl, phenyl, quinolinyl, pyridyl, furanyl, thienyl, C$_{1-6}$-alkoxy, Br, F, or Cl.

14. A method of preventing infection by influenza virus, comprising administering to a mammal in need of such treatment, an effective amount of the formula

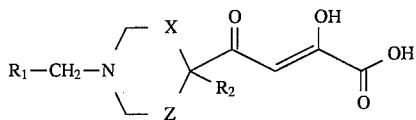

or pharmaceutically acceptable salt, hydrate or crystal form thereof, wherein:

X is —CH$_2$—, CH$_2$—CH$_2$—, or a bond;

Z is —CH$_2$—, CH$_2$—CH$_2$—, or a bond;

R$_1$ is
(i) phenyl, unsubstituted or substituted with halo; or
(ii) cyclohexyl;

R$_2$ is
(i) H or
(ii) benzyl, unsubstituted or substituted with halo.

15. A method of preventing infection by influenza virus, comprising administering to a mammal in need of such treatment, an effective amount of a compound of the structure

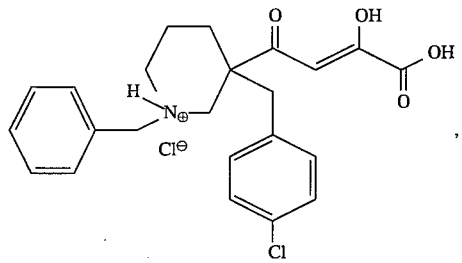

named

4-[N-benzyl-3-(4-chlorobenzyl)piperidin-3-yl]2,4-dioxobutanoic acid hydrochloride, or pharmaceutically acceptable salt, hydrate or ester thereof.

16. A method of preventing infection by influenza virus, comprising administering to a mammal in need of such treatment, an effective amount of a compound of the structure

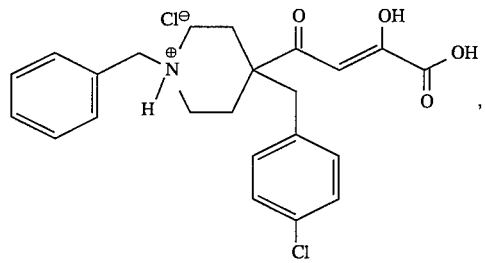

named

4-[N-benzyl-4-(p-chlorobenzyl)piperidin-4-yl]2,4-dioxobutanoic acid hydrochloride, or pharmaceutically acceptable salt, hydrate or ester thereof.

17. A method of preventing infection by influenza virus, comprising administering to a mammal in need of such treatment, an effective amount of a compound of the structure

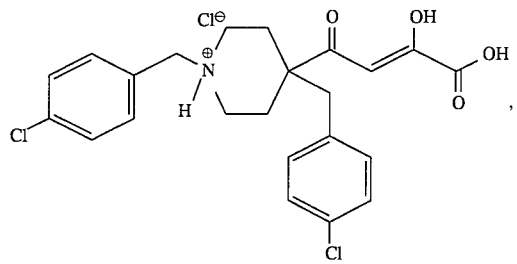

named

4-N-(p-chlorobenzyl)-4-(p-chlorobenzyl)piperidin-4-yl]
2,4-dioxobutanoic acid hydrochloride, or pharmaceutically acceptable salt, hydrate or ester thereof.

18. A method of preventing infection by influenza virus, comprising administering to a mammal in need of such treatment, an effective amount of a compound of the structure

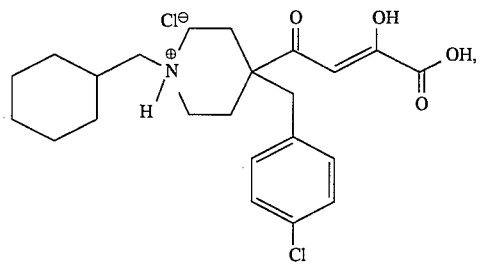

named

4-[1-cyclohexylmethyl-4-(p-chlorobenzyl)piperidin-4-yl]
2,4-dioxobutanoic acid hydrochloride, or pharmaceutically acceptable salt, hydrate or ester thereof.

19. A method of inhibiting influenza virus cap-dependent endonuclease, comprising administering to a mammal in need of such treatment, an effective amount of a compound of the formula

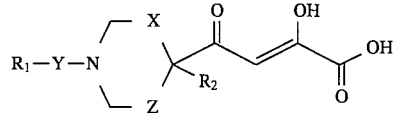

pharmaceutically acceptable salt, hydrate or crystal form thereof, wherein:

X is —CH$_2$—, CH$_2$—CH$_2$—, or a bond;

Z is —CH$_2$—, CH$_2$—CH$_2$—, or a bond;

Y is —CH$_2$—, CO, SO$_2$—, or a bond;

R$_1$ and R$_2$ are independently selected from the following:
branched or unbranched C$_{1-6}$ alkyl-, C$_{1-6}$ alkyloxy-, —N—C$_{1-6}$ alkyl-, C$_{3-8}$ cycloalkyl-, phenyl, naphthyl, pyridyl, furanyl, thienyl, or quinolinyl, any of which may be substituted once or twice with C$_{1-5}$ alkyl, C$_{3-8}$ cycloalkyl, phenyl, quinolinyl, pyridyl, furanyl, thienyl, C$_{1-6}$-alkoxy, Br, F, or Cl.

20. A method of inhibiting influenza virus cap-dependent endonuclease, comprising administering to a mammal in need of such treatment, an effective amount of a compound of the structure

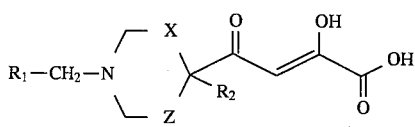

or pharmaceutically acceptable salt, hydrate or crystal form thereof,
wherein:
X is —CH$_2$—, CH$_2$—CH$_2$—, or a bond;
Z is —CH$_2$—, CH$_2$—CH$_2$—, or a bond;
R$_1$ is
  (i) phenyl, unsubstituted or substituted with halo; or
  (ii) cyclohexyl;
R$_2$ is
  (i) H or
  (ii) benzyl, unsubstituted or substituted with halo.

21. A method of inhibiting influenza virus cap-dependent endonuclease, comprising administering to a mammal in need of such treatment, an effective amount of a compound of the structure

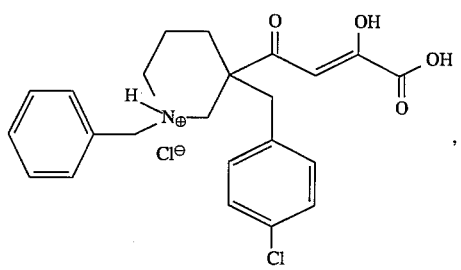

named

4-[N-benzyl-3-(4-chlorobenzyl)piperidin-3-yl]2,4-dioxobutanoic acid hydrochloride, or pharmaceutically acceptable salt, hydrate or ester thereof.

22. A method of inhibiting influenza virus cap-dependent endonuclease, comprising administering to a mammal in need of such treatment, an effective amount of a compound of the structure

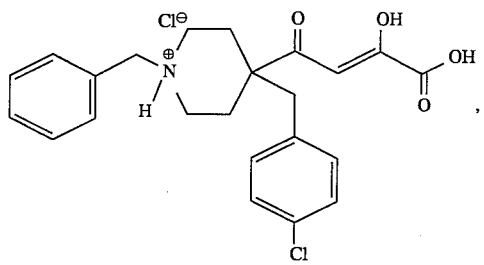

named

4-[N-benzyl-4-(p-chlorobenzyl)piperidin-4-yl]2,4-dioxobutanoic acid hydrochloride, or pharmaceutically acceptable salt, hydrate or ester thereof.

23. A method of inhibiting influenza virus cap-dependent endonuclease, comprising administering to a mammal in need of such treatment an effective amount of a compound of the structure

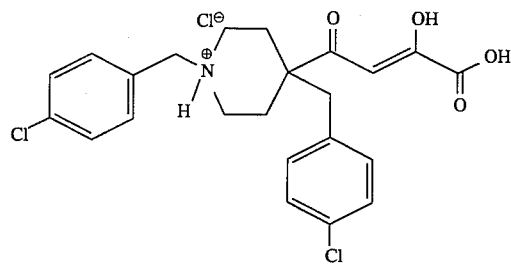

named

4-N-(p-chlorobenzyl)-4-(p-chlorobenzyl)piperidin-4-yl] 2,4-dioxobutanoic acid hydrochloride, or pharmaceutically acceptable salt, hydrate or ester thereof.

24. A method of inhibiting influenza virus cap-dependent endonuclease, comprising administering to a mammal in need of such treatment, an effective amount of a compound of the structure

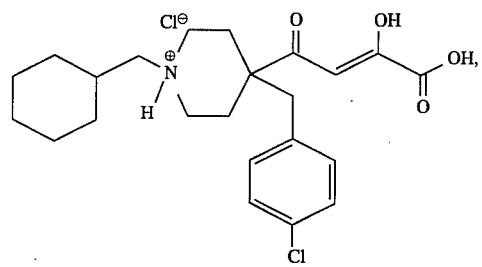

named

4-[1-cyclohexylmethyl-4-(p-chlorobenzyl)piperidin-4-yl] 2,4-dioxobutanoic acid hydrochloride, or pharmaceutically acceptable salt, hydrate or ester thereof.

* * * * *